United States Patent
Krauss

(10) Patent No.: US 11,298,097 B2
(45) Date of Patent: Apr. 12, 2022

(54) AUTOMATED DETERMINATION OF AN X-RAY TUBE-CURRENT PROFILE

(71) Applicant: Siemens Healthcare GmbH, Erlangen (DE)

(72) Inventor: Andreas Krauss, Bubenreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/217,032

(22) Filed: Mar. 30, 2021

(65) Prior Publication Data

US 2021/0307715 A1    Oct. 7, 2021

(30) Foreign Application Priority Data

Apr. 7, 2020   (DE) .................... 10 2020 204 515.1

(51) Int. Cl.
*A61B 6/00*    (2006.01)
*A61B 6/03*    (2006.01)

(52) U.S. Cl.
CPC ............. *A61B 6/54* (2013.01); *A61B 6/488* (2013.01); *A61B 6/5205* (2013.01)

(58) Field of Classification Search
CPC ......... A61B 6/032; A61B 6/542; A61B 6/488; A61B 6/5205; A61B 6/54; A61B 6/469; A61B 6/466
See application file for complete search history.

(56) References Cited

U.S. PATENT DOCUMENTS

2006/0269039 A1   11/2006   Raupach et al.
2008/0107231 A1   5/2008   Miyazaki et al.
(Continued)

FOREIGN PATENT DOCUMENTS

CN       1857164 A     11/2006
CN     101128153 A      2/2008
(Continued)

OTHER PUBLICATIONS

German Office Action for German Application No. 10 2020 204 515.1 dated Dec. 23, 2020.
(Continued)

*Primary Examiner* — Don K Wong
(74) *Attorney, Agent, or Firm* — Harness, Dickey & Pierce, P.L.C.

(57) ABSTRACT

A method is described for controlling a tube current for acquiring at least one X-ray image. The method includes performing a preview acquisition of the region under examination; determining a three-dimensionally modulated X-ray attenuation of the region based upon the preview acquisition; determining initial tube-current profiles based upon the X-ray attenuation; defining a tolerance band for subsequent real-time modification of tube currents, a maximum permitted tube-current profile being determined for which an X-ray tube of the X-ray imaging apparatus does not overheat; determining an expected value and a maximum value of a potential patient dose based upon the initial tube-current profiles and the tolerance band; measuring an actual X-ray attenuation during acquisition of the at least one X-ray image; determining adjusted tube-current profiles based upon the actual X-ray attenuation and the initial tube-current profiles; and adjusting the tube current in accordance with the adjusted tube-current profiles determined.

20 Claims, 4 Drawing Sheets

(56) References Cited

U.S. PATENT DOCUMENTS

| | | |
|---|---|---|
| 2009/0168951 A1 | 7/2009 | Yan |
| 2015/0327825 A1 | 11/2015 | Suzuki et al. |
| 2016/0262714 A1 | 9/2016 | Krauss et al. |
| 2018/0049714 A1* | 2/2018 | Nett .................. A61B 6/488 |
| 2019/0099148 A1 | 4/2019 | Rupcich et al. |
| 2019/0214135 A1 | 7/2019 | Wu et al. |
| 2021/0209818 A1 | 7/2021 | Travish et al. |

FOREIGN PATENT DOCUMENTS

| | | |
|---|---|---|
| CN | 101382505 A | 3/2009 |
| CN | 101472381 A | 7/2009 |
| CN | 108601572 A | 9/2018 |
| DE | 102015204449 A1 | 9/2016 |
| DE | 102018123517 A1 | 4/2019 |
| EP | 1172069 A1 | 1/2002 |

OTHER PUBLICATIONS

German Office Action for German Application No. 10 2020 204 515.1 dated Feb. 18, 2021.

German Office Action and English translation thereof dated Dec. 17, 2020.

German Decision to Grant and English translation thereof dated Feb. 15, 2021.

\* cited by examiner

AUTOMATED DETERMINATION OF AN X-RAY TUBE-CURRENT PROFILE

PRIORITY STATEMENT

The present application hereby claims priority under 35 U.S.C. § 119 to German patent application number DE 102020204515.1 filed Apr. 7, 2020, the entire contents of which are hereby incorporated herein by reference.

FIELD

Example embodiments of the invention generally relate to a method for controlling a tube current for acquiring at least one X-ray image of a region under examination of a subject under examination using an X-ray imaging apparatus. Example embodiments of the invention also generally relate to a tube-current controller. In addition, example embodiments of the invention also generally relates to an X-ray imaging apparatus. Example embodiments of the invention also generally relates to a computed tomography system.

BACKGROUND

Imaging X-ray equipment such as a C-arm X-ray apparatus or a computed tomography apparatus, for instance, are being used increasingly to resolve medical questions. The X-ray radiation results in mounting radiation exposure for patients, and therefore it is a requirement for every examination that usage is appropriate and dose-optimized in accordance with the ALARA principle ("as low as reasonably achievable"). It is hence the aim of medical imaging to give a patient the minimum possible dose of X-ray radiation for generating one or more X-ray images.

With this aim in mind, modern CT scanners automatically adjust tube currents, and hence the dose, according to the attenuation characteristics of the patient under examination. CARE Dose4D, for example, is one such automatic dose control system. In order to determine the attenuation characteristics of a patient, the patient attenuation profiles in the anterior/posterior direction and the lateral direction must be known accurately before starting the actual image acquisition.

Known automatic dose control systems are based on topograms. A topogram is equivalent to a conventional two-dimensional X-ray superimposition acquisition. It measures the individual X-ray attenuation distribution through a patient in a particular projection direction in which the X-ray radiation passes through the patient, and represents this distribution by way of different gray-scale values. An automatic dose control system uses this X-ray attenuation to determine a suitable tube-current profile, or to modulate the tube current. It is known to acquire one topogram of a patient in the lateral direction and one in the anterior/posterior direction before an X-ray image acquisition, and to determine the X-ray attenuation distribution for the patient in each direction based upon the gray-scale value distribution.

It is also possible to estimate a patient attenuation using an optical 3D camera. For example, DE 102015204449 and US 2019/0214135 describe such a procedure.

If only one topogram is produced, there are likely to be inaccuracies in the estimate of the patient attenuation if the patient is not positioned optimally in the center of rotation of the scanner. Even when the patient is optimally centered, patient movements between topogram scan and tomogram scan can cause inaccuracies. For example, this can occur as a result of different respiratory states for the topogram and the tomogram.

When using an optical 3D camera, inaccuracies arise because of clothing or covers and also on account of the non-trivial relationship between the patient surface and the patient attenuation.

The aforementioned inaccuracies in the estimate of the patient attenuation prior to the actual X-ray image acquisition result in a sub-optimum X-ray dose for the patient.

EP 1172069 A1 describes what is known as a CT automatic exposure control system, in which the tube current is controlled in real time in order to achieve a predefined image noise.

SUMMARY

The inventors have discovered that it is not possible, in the above-mentioned method, to take into account technical limitations of the X-ray tube such as the inertia of the tube-current modulation or overheating of the tube in the event of overload, for instance. In addition, the above-mentioned method described does not allow the dose given to the patient to be estimated before performing the scan.

At least one embodiment of the present invention is directed to achieving improved accuracy when adjusting the X-ray tube-current profile in accordance with the personal X-ray attenuation characteristics of a patient, while allowing a further reduction in the overall dose given to the patient.

Embodiments of the invention are directed to a method for controlling a tube current for acquiring at least one X-ray image of a region under examination of a subject under examination using an X-ray imaging apparatus; a tube-current controller; an X-ray imaging apparatus; and a computed tomography system.

In the method according to an embodiment of the invention for controlling a tube current for acquiring at least one X-ray image of a region under examination of a subject under examination using an X-ray imaging apparatus, a preview acquisition of the region under examination of the subject under examination is performed. The preview acquisition is used to obtain information about the X-ray attenuation that will occur during the subsequent actual X-ray image acquisition. In other words, a three-dimensionally modulated X-ray attenuation of the region under examination is determined based upon the preview acquisition. In this context, the region under examination shall comprise the region of the subject under examination that is subsequently exposed to X-ray radiation during the actual X-ray image acquisition. For instance, this region can comprise a segment of a patient body, or even the entire body of a patient for a whole-body examination.

The tube-current controller according to an embodiment of the invention for acquiring at least one X-ray image of a region under examination of a subject under examination comprises a control unit for controlling an X-ray radiation source for an X-ray image acquisition and for capturing raw X-ray data from an X-ray radiation detector. A preview-acquisition control unit for controlling a preview acquisition of the region under examination of the subject under examination is also part of the tube-current controller according to an embodiment of the invention. The tube-current controller also comprises an X-ray attenuation estimation unit for estimating a three-dimensionally modulated X-ray attenuation based upon the preview acquisition. In addition, the tube-current controller according to an embodiment of the invention comprises a profile definition unit for determining initial tube-current profiles based upon the estimated X-ray attenuation.

The X-ray imaging apparatus according to an embodiment of the invention comprises an X-ray radiation source having an X-ray tube, and comprises an X-ray radiation detector and the tube-current controller according to an embodiment of the invention. The X-ray imaging apparatus according to an embodiment of the invention shares the advantages of the tube-current controller according to an embodiment of the invention.

At least one embodiment of the invention is also directed to a corresponding computer program product comprising a computer program, which can be loaded directly into a storage device of an X-ray imaging apparatus and/or of a storage device of a controller of a computed tomography system and which contains program segments in order to perform all the steps of the method according to an embodiment of the invention when the computer program is executed in the controller of the X-ray imaging apparatus and/or in the controller of the computed tomography system.

At least one embodiment of the invention is also directed to a method for controlling a tube current for acquiring at least one X-ray image of a region under examination of a subject under examination using an X-ray imaging apparatus, comprising:

performing a preview acquisition of the region under examination of the subject under examination;

determining a three-dimensionally modulated X-ray attenuation of the region under examination based upon the preview acquisition;

determining initial tube-current profiles based upon the three-dimensionally modulated X-ray attenuation determined;

defining a tolerance band for subsequent real-time modification of tube currents, wherein, based upon initial tube-current profiles, a maximum permitted tube-current profile is determined for which an X-ray tube of the X-ray imaging apparatus does not overheat;

determining an expected value and a maximum value of a potential patient dose based upon the initial tube-current profiles and the tolerance band defined;

measuring an actual X-ray attenuation during acquisition of the at least one X-ray image;

determining adjusted tube-current profiles based upon the actual X-ray attenuation and the initial tube-current profiles; and adjusting the tube current in accordance with the adjusted tube-current profiles determined.

At least one embodiment of the invention is also directed to a tube-current controller for acquiring at least one X-ray image of a region under examination of a subject under examination, comprising:

a controller configured to
control an X-ray radiation source for acquisition of the at least one X-ray image, and
capture raw X-ray data from an X-ray radiation detector;
a preview acquisition controller to control a preview acquisition of the region under examination of the subject under examination;
an X-ray attenuation estimation unit to estimate a three-dimensionally modulated X-ray attenuation based upon the preview acquisition;
a profile definition unit to determine initial tube-current profiles based upon the X-ray attenuation estimated;
a band definition unit to define a tolerance band for real-time modification of tube currents, wherein, based upon the initial tube-current profiles, a maximum permitted tube-current profile is determined for which the X-ray tube does not overheat;
a dose determination unit to determine an expected value for a potential patient dose based upon the initial tube-current profiles, and a maximum value of a potential patient dose based upon the defined tolerance band;
an X-ray attenuation determination unit to determine an actual X-ray attenuation during acquisition of the at least one X-ray image based upon raw X-ray data acquired; and
an adjustment unit to determine adjusted tube-current profiles based upon the actual X-ray attenuation and initially planned tube-current profiles,
wherein the controller is further configured to adjust the tube current of the X-ray source in accordance with the adjusted tube-current profiles determined.

At least one embodiment of the invention is also directed to an x-ray imaging apparatus, comprising:
an X-ray radiation source including an X-ray tube;
an X-ray radiation detector; and
the tube-current controller of an embodiment.

At least one embodiment of the invention is also directed to a computed tomography system comprising the X-ray imaging apparatus of an embodiment.

At least one embodiment of the invention is also directed to a non-transitory computer program product storing a computer program, directly loadable into a storage device of an X-ray imaging apparatus, including program segments to perform the method of an embodiment when the computer program is executed in the X-ray imaging apparatus.

At least one embodiment of the invention is also directed to a non-transitory computer-readable medium, storing program segments, readable and executable by a processor to perform the method of an embodiment when the program segments are executed by the processor.

BRIEF DESCRIPTION OF THE DRAWINGS

The invention is described and explained in greater detail below with reference to the example embodiments shown in the figures,
in which.

DETAILED DESCRIPTION OF THE EXAMPLE EMBODIMENTS

Figure 1:
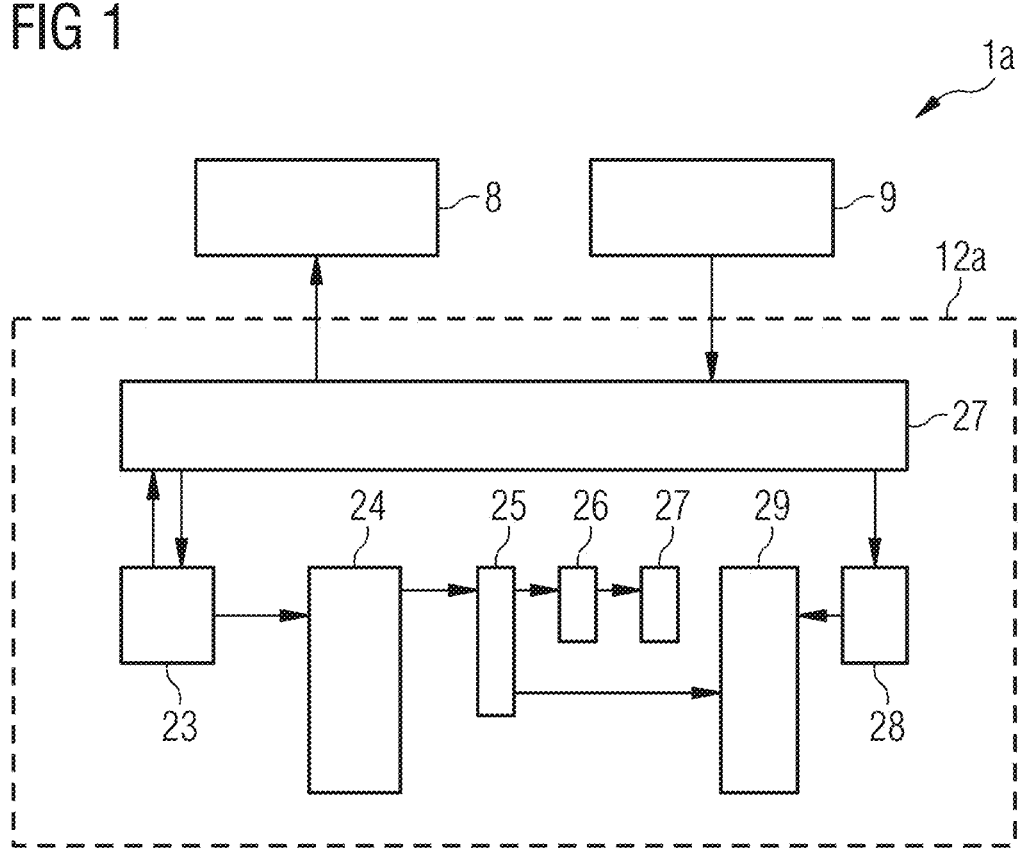
FIG. 1 shows a schematic diagram of an X-ray imaging apparatus comprising a tube controller according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature (s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules.

Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In the method according to an embodiment of the invention for controlling a tube current for acquiring at least one X-ray image of a region under examination of a subject under examination using an X-ray imaging apparatus, a preview acquisition of the region under examination of the subject under examination is performed. The preview acquisition is used to obtain information about the X-ray attenuation that will occur during the subsequent actual X-ray image acquisition. In other words, a three-dimensionally modulated X-ray attenuation of the region under examination is determined based upon the preview acquisition. In this context, the region under examination shall comprise the region of the subject under examination that is subsequently exposed to X-ray radiation during the actual X-ray image acquisition. For instance, this region can comprise a segment of a patient body, or even the entire body of a patient for a whole-body examination.

Initial tube-current profiles are then calculated based upon the determined X-ray attenuation. The initial tube-current profiles are determined so as to achieve a predefined signal-to-noise ratio and an associated image quality. In addition, a tolerance band is defined for subsequent real-time modification of tube currents, wherein a maximum permitted tube-current profile is determined for which the X-ray tube does not overheat. The tube-current profiles adjusted during the subsequent X-ray imaging must therefore not exceed the defined maximum. In this context, a tube-current profile shall be understood to mean a current/time curve that represents the tube current produced by an X-ray tube over the examination time or at least over a predetermined time interval of an examination, or represents the corresponding time-dependent current magnitude.

In addition, an expected value for a potential patient dose is determined based upon the initial tube-current profiles $Iap(z)$, $Ilat(z)$, and a maximum value of a potential patient dose is determined based upon the defined tolerance band. The subsequent adjustment of the tube currents during the actual X-ray imaging can take account of the maximum value, for example, by appropriate limits to the tolerance band being set in advance such that a maximum dose is not exceeded. It is also possible during the X-ray imaging, however, to determine an X-ray dose already given and to set sliding and variable limits to the tolerance band in real time based upon the X-ray dose predicted to be required for the remaining X-ray imaging process.

During the actual X-ray image acquisition, an actual X-ray attenuation is then determined regularly based upon the measured raw data or projections. The X-ray attenuation is preferably calculated by simple division of the logarithm of the attenuation data by the linear absorption coefficient of water.

Adjusted tube-current profiles are then calculated based upon the actual X-ray attenuation values and the initially planned tube-current profiles. This is because the actual X-ray attenuation values provide information on how far the previously made estimate of the X-ray attenuations departs from the actual value. Finally, the tube current is adjusted in accordance with the determined adjusted tube-current profiles. The adjustment and the steps for determining the actual X-ray attenuation of the subject under examination can be performed repeatedly, or updated, during the X-ray imaging in order to achieve a high-quality X-ray acquisition for a minimum X-ray dose.

The tube-current controller according to an embodiment of the invention for acquiring at least one X-ray image of a region under examination of a subject under examination comprises a control unit for controlling an X-ray radiation source for an X-ray image acquisition and for capturing raw X-ray data from an X-ray radiation detector. A preview-acquisition control unit for controlling a preview acquisition of the region under examination of the subject under examination is also part of the tube-current controller according to the invention. The tube-current controller also comprises an X-ray attenuation estimation unit for estimating a three-dimensionally modulated X-ray attenuation based upon the preview acquisition. In addition, the tube-current controller according to an embodiment of the invention comprises a profile definition unit for determining initial tube-current profiles based upon the estimated X-ray attenuation.

In order to take into account technical limitations, the tube-current controller according to an embodiment of the invention also comprises a band definition unit for defining a tolerance band for subsequent real-time modification of tube currents, wherein a maximum permitted tube-current profile is determined for which the X-ray tube does not overheat.

To protect the patient from an excessive dose, the tube-current controller according to the invention comprises a dose determination unit for determining an expected value based upon the initial tube-current profiles, and a maximum value of a potential patient dose based upon the defined tolerance band.

An X-ray attenuation determination unit for determining an actual X-ray attenuation during an X-ray image acquisition based upon the acquired raw X-ray data is also part of the tube-current controller according to an embodiment of the invention.

The tube-current controller according to an embodiment of the invention also comprises an adjustment unit for determining adjusted tube-current profiles based upon the actual X-ray attenuation and the initially planned tube-current profiles. The control unit is configured to adjust the tube current of the X-ray source in accordance with the determined adjusted tube-current profiles. The tube-current controller according to the invention shares the advantages of the method according to an embodiment of the invention for controlling a tube current.

The X-ray imaging apparatus according to an embodiment of the invention comprises an X-ray radiation source having an X-ray tube, and comprises an X-ray radiation detector and the tube-current controller according to an embodiment of the invention. The X-ray imaging apparatus according to an embodiment of the invention shares the advantages of the tube-current controller according to an embodiment of the invention.

The X-ray imaging apparatus may be part of an X-ray apparatus that is designed to acquire a multiplicity of X-ray projections from different projection angles, for instance a computed tomography apparatus having an annular rotating frame, or a C-arm X-ray apparatus. The acquisitions can be produced during a, in particular continuous, rotational movement of an acquisition unit comprising an X-ray radiation source and an X-ray radiation detector, which interacts with the X-ray radiation source. The X-ray radiation source in particular may be a rotating anode X-ray tube. The X-ray radiation detector for a computed tomography apparatus is a multiple-row detector, for example. An example of an X-ray detector for a C-arm X-ray apparatus is a flat-panel detector. Both an energy-resolving design and a counting design are possible for the X-ray detector.

Most of the essential components of the tube-current controller according to an embodiment of the invention can be embodied in the form of software components. This relates in particular to the control unit, the preview acquisition control unit for controlling a preview acquisition of the region under examination of the subject under examination, the X-ray attenuation estimation unit for estimating a three-dimensionally modulated X-ray attenuation based upon the preview acquisition, the profile definition unit, the band definition unit, the dose determination unit, the X-ray attenuation determination unit, and the adjustment unit.

In principle, however, some of these components can also be implemented in the form of software-aided hardware, for instance FPGAs or the like, in particular when especially fast calculations are needed. Likewise, the required interfaces can be designed as software interfaces, for instance if all that is involved is a transfer of data from other software components. They can also be designed, however, as hardware-built interfaces driven by suitable software.

An implementation largely in software has the advantage that even controllers already in use for X-ray imaging apparatuses, for instance computed tomography systems, can be easily upgraded by a software update in order to work in the manner according to an embodiment of the invention.

In this respect, at least one embodiment of the invention is also directed to a corresponding computer program product comprising a computer program, which can be loaded directly into a storage device of an X-ray imaging apparatus and/or of a storage device of a controller of a computed tomography system and which contains program segments in order to perform all the steps of the method according to an embodiment of the invention when the computer program is executed in the controller of the X-ray imaging apparatus and/or in the controller of the computed tomography system.

The computer program product may comprise in addition to the computer program, if applicable, extra elements such as e.g. documentation and/or extra components, including hardware components, such as e.g. hardware keys (dongles etc.) for using the software.

By virtue of a software implementation, the method can be performed reproducibly on different computers with less susceptibility to errors.

For transfer to the storage device of the image-data generation device and/or controller of the computed tomography system, and/or for storage on the image-data generation device and/or the controller of the computed tomography system, a computer-readable medium, for instance a memory stick, a hard disk or any other portable or permanently installed data storage medium can be used, on which are stored the program segments of the computer program, which program segments can be downloaded and executed by a processing unit of the X-ray imaging apparatus. For this purpose, the processing unit can comprise, for example, one or more interacting microprocessors or the like.

The claims and the following description each contain particularly advantageous embodiments and developments of the invention. In particular, the claims in one category of claims can also be developed in a similar way to the dependent claims in another category of claims. Furthermore, within the scope of the invention, the various features of different example embodiments and claims can also be combined to create new example embodiments.

According to an embodiment of the method according to the invention, the preview acquisition comprises a topogram of the region under examination of the subject under examination. The method according to an embodiment of the invention can improve the accuracy of an automatic dose control system based on a topogram for a patient who is not centrally positioned.

According to one aspect of the method according to an embodiment of the invention, the preview acquisition comprises an optical image acquisition of the region under examination of the subject under examination. If the preview acquisition is performed without a topogram based upon a relatively inaccurate estimate of the X-ray attenuation using data from an optical sensor such as a camera, for instance, then the method according to an embodiment of the invention achieves a significant improvement in the accuracy of an automatic dose control system. In order to acquire an image of the subject under examination, the X-ray imaging apparatus preferably comprises an optical sensor at least in the body region to be imaged.

In a particularly practical variant of the method according to an embodiment of the invention, determining the three-dimensionally modulated X-ray attenuation comprises determining X-ray attenuation vectors.

The X-ray attenuation vectors are preferably determined in the anterior/posterior direction and in the lateral direction by way of the preview acquisition. If the subject under examination is a patient, it can be assumed that in the transverse plane, the patient has the smallest dimensions in the anterior/posterior direction, and the largest dimensions in the lateral direction. Hence the lowest X-ray attenuation can also be expected for the X-ray projection in the anterior/posterior direction, and the strongest X-ray attenuation can be presumed in the lateral direction. The two estimated values for the X-ray attenuation in the anterior/posterior direction and in the lateral direction can therefore be adopted as a minimum value and a maximum value, between which the X-ray attenuation varies in a continuous transition. The analysis of the preview acquisition can advantageously be confined to a small number of directions, thereby reducing the computational effort.

Hence the initial tube-current profiles can then also be determined based upon the determined X-ray attenuation in the anterior/posterior direction and in the lateral direction.

In addition, the actual X-ray attenuation is measured particularly preferably in the anterior/posterior direction and in the lateral direction, because, as already mentioned, it is in these directions that the boundary values of a value range of the possible X-ray attenuation values are expected. The calculation of the actual X-ray tube-current profile can advantageously be simplified by selecting just two particularly meaningful directions, whereby it is also possible to implement more easily a real-time function for adapting the tube-current profile.

In order to comply with the maximum patient dose, a maximum permitted increase in the patient dose by way of a configurable parameter is preferably displayed to the operator during the X-ray image acquisition. In this variant, a variation parameter and its range of variation for adapting the tube current is predefined.

Alternatively, the value range of the range of variation can also be adjusted in real time during an X-ray acquisition according to the X-ray dose already given and according to the X-ray dose expected over the course of the further X-ray imaging. In this variant, a maximum image quality can be achieved while complying with the permitted or specified X-ray dose.

The tube currents are preferably adjusted based upon a function for adjusting the initially planned tube currents that comprises an exponential function of a product of the absorption coefficient of water and the difference between the actual patient attenuation and the X-ray attenuation vectors determined based upon the preview acquisition.

In a CT system, the tube currents are preferably adjusted at a delay of 180°. In other words, the correction to the tube currents at a particular position z of a CT spiral scan is based on the measurement of the patient attenuation in the previous half-revolution of the gantry. This achieves maximum currency of the data forming the basis of the tube-current adjustment.

FIG. 1 shows schematically an X-ray imaging apparatus 1a comprising a tube controller 12a according to an example embodiment of the invention. The X-ray imaging apparatus 1a comprises also an X-ray source 8 and an X-ray detector 9 in addition to the tube-current controller 12a.

The X-ray tube controller 12a comprises a preview acquisition control unit 23 for controlling a preview acquisition of a region under examination of a subject under examination. That is to say, the preview acquisition control unit 23 is used to control a control unit 27, by which the X-ray radiation source 8 is controlled for an X-ray image acquisition and for a preview acquisition. In addition, the control unit 27 is also configured to capture raw X-ray data from an X-ray radiation detector 9. An X-ray attenuation estimation unit 24, which is configured to determine X-ray attenuation vectors Wap(z), Wlat(z) in the anterior/posterior direction and in the lateral direction based upon the topogram, is also part of the X-ray tube controller 12a. The determined X-ray attenuation vectors Wap(z), Wlat(z) are then used by a profile definition unit 25 to calculate initial tube-current profiles Iap(z), Ilat (z).

The tube controller 12a also comprises a band definition unit 26. The band definition unit is used to define a tolerance band for subsequent real-time modification of tube currents. This tolerance band defines a maximum permitted tube current or a maximum permitted tube-current profile for which the X-ray tube still does not overheat.

Based upon the initial tube-current profiles Iap(z), Ilat(z), it is now possible to define in advance the amount of adjustment to a tube current, if applicable, that is permitted during an X-ray image acquisition.

A dose determination unit 27, which is configured to determine an expected value and a maximum value of a potential patient dose based upon the initial tube-current profiles Iap(z), Ilat(z) and the defined tolerance band, is also part of the X-ray tube controller 12a. In other words, an expected value of an X-ray dose for the patient can be calculated based upon the initial tube-current profiles Iap(z), Ilat(z). The maximum value is then obtained from the defined tolerance band. If the maximum value is higher than a specified X-ray dose, then appropriate limits to the tolerance band can be set to avoid exceeding the specified X-ray dose value.

The X-ray tube controller 12a also comprises an X-ray attenuation determination unit 28, which is configured to determine an actual X-ray attenuation Vap, Vlat in the anterior/posterior direction and in the lateral direction during an X-ray image acquisition, based upon the acquired raw X-ray data. Projections in tube positions 3 o'clock, 9 o'clock and 6 o'clock, 12 o'clock are analyzed for determining the actual X-ray attenuation in the anterior/posterior direction and in the lateral direction. The positions are labeled in FIG. 2 with "3 h", "9 h", "6 h" and "12 h".

The actual X-ray attenuation can be determined by simple division of the logarithm of the attenuation values of a projection by the linear absorption coefficient of water.

Based upon the actual X-ray attenuation and the initial tube-current profiles in the anterior/posterior direction and in the lateral direction, an adjustment unit 29, which is also part of the X-ray tube controller 12a, then determines adjusted tube-current profiles in the anterior/posterior direction and in the lateral direction.

The control unit 27 uses the adjusted tube-current profiles to adjust the tube current of the X-ray source 8 in accordance with the determined adjusted tube-current profiles.

Figure 2:
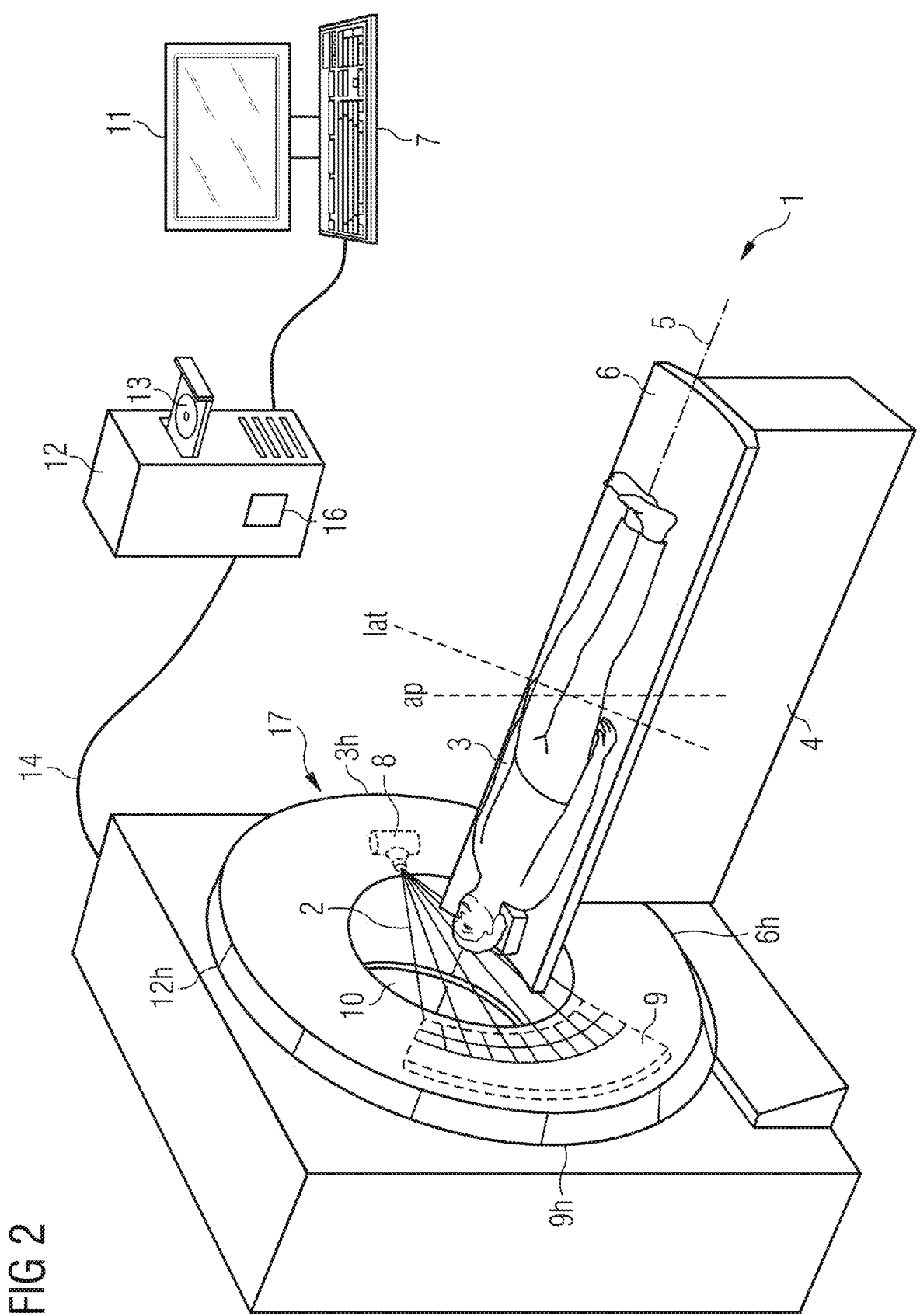
FIG. 2 shows a computed tomography system according to an example embodiment of the invention.

FIG. 2 shows an X-ray imaging apparatus 1 using the example of an X-ray computed tomography apparatus. The computed tomography apparatus shown here has an acquisition unit 17 comprising a radiation source 8 in the form of an X-ray source, and a radiation detector 9 in the form of an X-ray detector. The acquisition unit 17 rotates about a system axis 5 during the acquisition of X-ray projections, and the X-ray source 8 emits rays 2 in the form of X-rays during the acquisition. The X-ray source 8 is an X-ray tube. The X-ray detector is a multiple-row detector.

A patient 3 lies on a patient couch 6 during the acquisition of projections. The patient couch 6 is connected to a couch base 4 such that the base supports the patient couch 6 bearing the patient 3. The patient couch 6 is designed to move the patient 3 along an acquisition direction through the aperture 10 of the acquisition unit 17. The acquisition direction is usually defined by the system axis 5, which is oriented in the z-direction. During the acquisition of X-ray projections, the acquisition unit 17 rotates about the z-axis. In this example, the body axis of the patient is the same as the system axis 5. Both axes lie on the z-axis of a three-dimensional Cartesian coordinate system. For a spiral acquisition, the patient couch 6 is moved continuously through the aperture 10 while the acquisition unit 17 rotates about the patient 3 and acquires X-ray projections. The X-rays thus describe a spiral on the surface of the patient 3.

The X-ray imaging apparatus 1 has a computer 12, which is connected to a display unit 11, for instance for the graphical display of X-ray acquisitions, and to an input unit 7. The display unit 11 may be an LCD, plasma or OLED screen, for instance. It may also be a touchscreen, which is also embodied as the input unit 7. Such a touchscreen may be integrated in the imaging device or be designed as part of a portable device. The input unit 7 is, for example, a keyboard, a mouse, a touchscreen or even a microphone for voice input. The input unit 7 can also be designed to detect and convert into suitable commands, movements of a user. A user can use the input unit 7 to modify, for example, a selected reference dataset that is used in preparing for an imaging.

The computer 12 is connected to the rotatable acquisition unit 17 for the purpose of data transfer. Via the connection 14, control signals for the X-ray image acquisition are transmitted from the computer 12 to the acquisition unit 17, and acquired projection data is transmitted to the computer 12 for image reconstruction. The connection 14 is implemented in wired or wireless form in a known manner.

The computer 12 comprises a processing unit 16. The processing unit 16 is embodied as an image processing unit or an image-data processing unit. It is configured to perform all the data processing steps relating to the method according to an embodiment of the invention. The processing unit 16 can interact with a computer-readable data storage medium 13, in particular in order to perform a method according to an embodiment of the invention via a computer program containing program code. In addition, the computer program can be stored in retrievable form on the computer-readable storage medium. The machine-readable storage medium can be in particular a CD, DVD, Blu-Ray disc, a memory stick or a hard disk. The processing unit 16 can be in the form of hardware or software. For example, the processing unit 16 is embodied as an FPGA (Field Programmable Gate Array) or comprises an arithmetic logic unit.

In the embodiment shown here, at least one computer program is stored in the memory of the computer 12, which computer program, when executed on the computer 12, performs all the method steps of the method according to an embodiment of the invention for controlling a tube current for acquiring at least one X-ray image of a region under examination of a subject under examination using an X-ray imaging apparatus. The computer program for performing the method steps of the method according to an embodiment of the invention comprises a program code. In addition, the computer program can be in the form of an executable file and/or can be stored in another processing system other than the computer 12. For example, the X-ray imaging apparatus 1 can be designed such that the computer 12 downloads the computer program for performing the method according to an embodiment of the invention to its internal main memory via an intranet or via the Internet.

Figure 3:
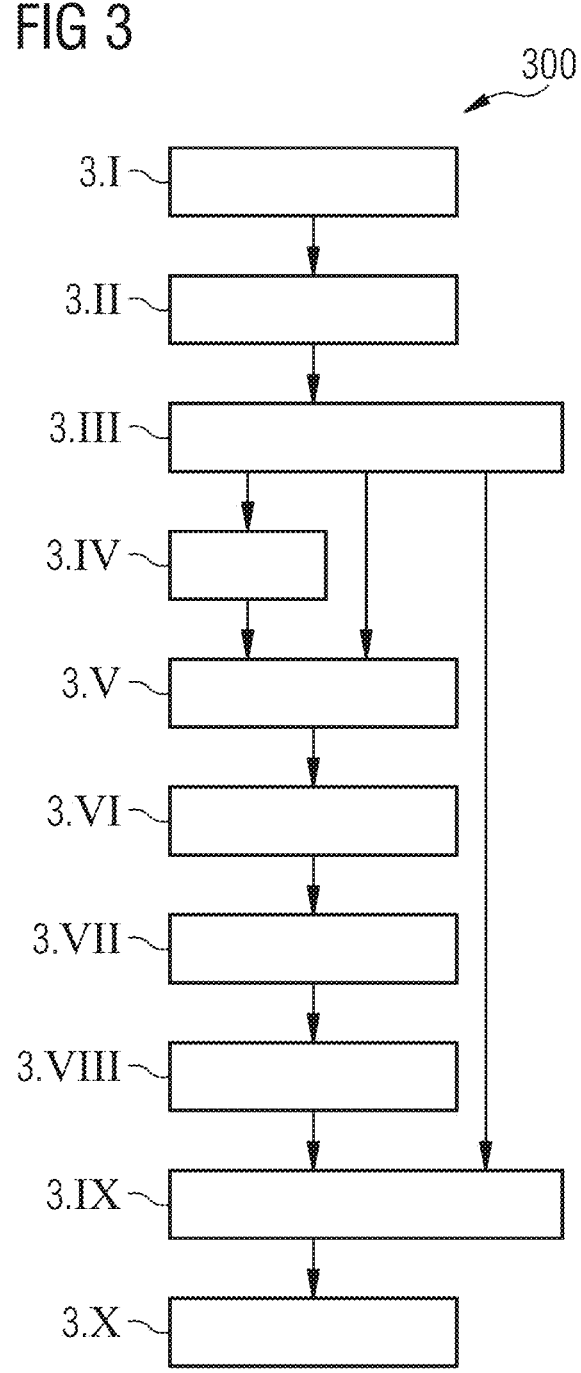
FIG. 3 shows a flow diagram of a method for controlling a tube current for acquiring an X-ray image of a region under examination of a subject under examination according to an example embodiment of the invention.

FIG. 3 shows a flow diagram illustrating a method for controlling a tube current for acquiring at least one X-ray image of a region under examination of a subject under examination using an X-ray imaging apparatus according to an example embodiment of the invention. In step 3.I, first a preview acquisition of the region under examination of the subject under examination, a patient in this example embodiment, is performed. The preview acquisition can be made in the form of a topogram, for example. In the case of a topogram, the acquisition unit of the X-ray imaging apparatus is used to produce X-ray image acquisitions from a plurality of directions. As an alternative, it is also possible to use optical sensors such as a camera, for instance, to acquire images of the patient from a plurality of directions in order to determine the dimensions of the patient in three dimensions.

In step 3.II, X-ray attenuation vectors $W_{ap}(z)$, $W_{lat}(z)$ in the anterior/posterior direction and in the lateral direction are determined based upon the generated preview acquisition. It can be assumed that a patient, for example, has the smallest dimensions in the anterior/posterior direction, and the largest dimensions in the lateral direction. In a subsequent X-ray image acquisition, the highest X-ray attenuation values can then be expected in the lateral direction, and the smallest X-ray attenuation values in the anterior/posterior direction. During a quarter-rotation of the acquisition unit, the X-ray attenuation value varies predictably between these two values.

In step 3.III, initial tube-current profiles $I_{ap}(z)$, $I_{lat}(z)$ in the anterior/posterior direction and in the lateral direction are calculated based upon the determined X-ray attenuation vectors $W_{ap}(z)$, $W_{lat}(z)$.

In addition, in step 3.IV, a tolerance band is determined for subsequent real-time modification of tube currents. This tolerance band must be selected such that a maximum permitted tube current is not exceeded, or else the X-ray tube will overheat. The tolerance band is determined based upon the initial tube-current profiles $I_{ap}(z)$, $I_{lat}(z)$.

In addition, in step 3.V, an expected value and a maximum value of a potential patient dose are calculated based upon the initial tube-current profiles $I_{ap}(z)$, $I_{lat}(z)$ and the defined tolerance band. In other words, the expected value of the X-ray dose is obtained from the initial tube-current profiles, which of course represent a time-dependent quantity. The maximum value of the potential patient dose, on the other hand, is obtained from the permitted tube current. In step 3.VI, to prevent the X-ray dose from now exceeding the dose permitted for health, limits to the tolerance band of the tube current are set such that the X-ray dose is not expected to exceed the dose allowed for health. As explained below, it is also possible to narrow the tolerance band based upon the actual tube-current profiles in real time during the X-ray imaging acquisition so as to be certain of preventing the X-ray dose exceeding the dose permitted for health in the event that the actual tube-current profiles diverge from the initial tube-current profiles.

In step 3.VII, the actual X-ray imaging of a region under examination of the patient is started. In step 3.VIII, an actual X-ray attenuation $V_{ap}$, $V_{lat}$ is determined during the X-ray image acquisition based upon the X-ray attenuation data captured in real time in the anterior/posterior direction and in the lateral direction.

In step 3.IX, adjusted tube-current profiles are then calculated based upon the actual patient attenuation and the initially planned tube-current profiles. The adjusted tube currents $J_{ap}(z)$, $J_{lat}(z)$ in the anterior/posterior direction and in the lateral direction are calculated using the absorption coefficient of water mu and a suitably selected parameter b (0<b<1) as follows:

$$J_{ap(z)} = I_{ap}(z) \cdot e^{mu \cdot b \cdot (v_{ap}(z) - w_{ap}(z))} \quad (1)$$

and $J_{lat}(z) = I_{lat}(z) \cdot e^{mu \cdot b \cdot (v_{lat}(z) - w_{lat}(z))}$. (2)

In step 3.X, a tube current is adjusted in accordance with the determined adjusted tube-current profiles.

Figure 4:
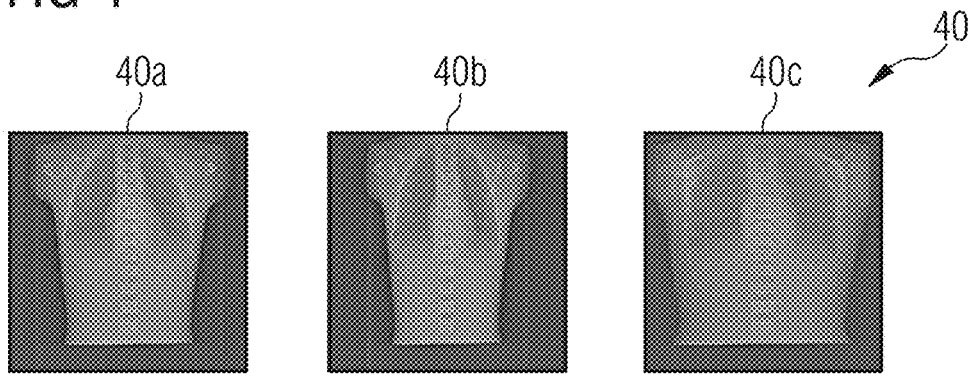
FIG. 4 shows topograms of a thorax phantom at different distances from the image acquisition unit.

FIG. 4 shows a comparison diagram 40 of three different topograms 40a, 40b, 40c in the anterior/posterior direction of a thorax phantom. The individual topograms 40a, 40b, 40c differ in that the thorax phantom is positioned differently. In the left-hand depiction 40a, the thorax phantom is in a central position relative to the circular gantry or acquisition unit (see FIG. 2). In the center depiction 40b, on the other hand, the thorax phantom is in a lower position, i.e. is at a greater distance from the X-ray source. The depiction of the thorax phantom is thereby smaller in size. The opposite effect can be seen in the right-hand depiction 40c. Here, the thorax phantom is positioned closer to the X-ray source, resulting in an enlarged representation of the thorax phantom.

Figure 5:
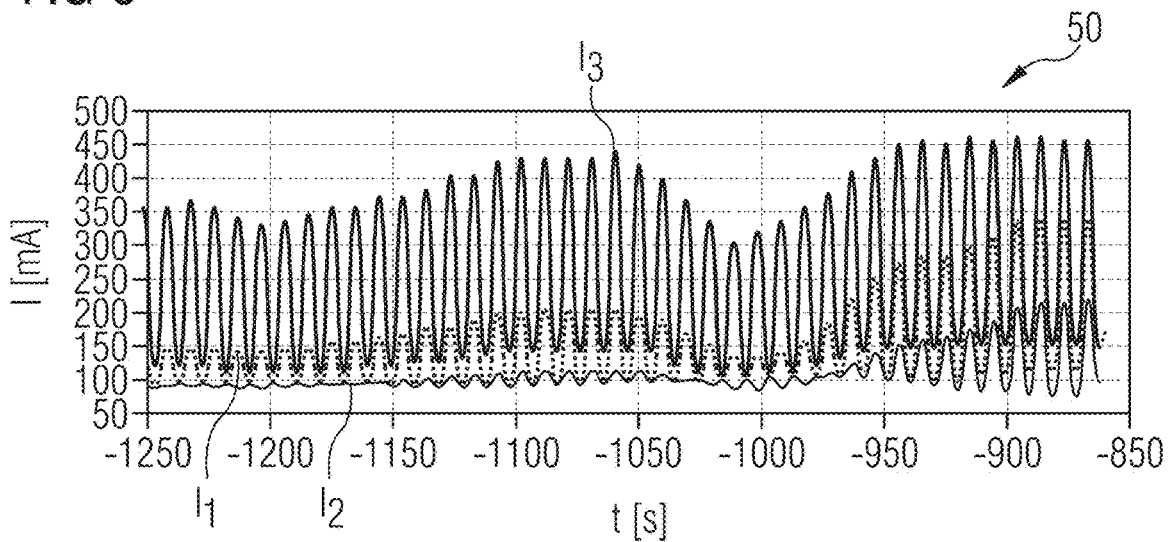
FIG. 5 shows a graph illustrating three different initial tube-current profiles for the three different topograms shown in FIG. 4.

The different topograms 40a, 40b, 40c result in the different initial tube currents or tube-current profiles shown in FIG. 5 as the basis for planning CT X-ray imaging. FIG. 5 presents a graph 50 that shows the profile of three different tube currents. The currents, or more precisely their current magnitudes I, are plotted in units of mA over time t. A tube-current profile $I_1$ is obtained from the left-hand topogram 40a. The center topogram 40b corresponds to a tube-current profile 12. It can be seen that the amplitudes of the tube current $I_2$ associated with the center topogram 40b are significantly lower than the amplitudes of the tube current $I_1$ associated with the left-hand topogram. A tube-current profile $I_3$ having by far the largest amplitudes is associated with the right-hand topogram 40c. If an X-ray image acquisition were now to be performed using the tube current $I_2$, which was determined by acquiring the center topogram 40b, then although the patient would receive only a low X-ray dose, a reduced image quality might result. In the case of the tube current $I_3$, which was determined by acquiring the right-hand topogram 40c, the patient would potentially receive too high an X-ray dose.

Figure 6:
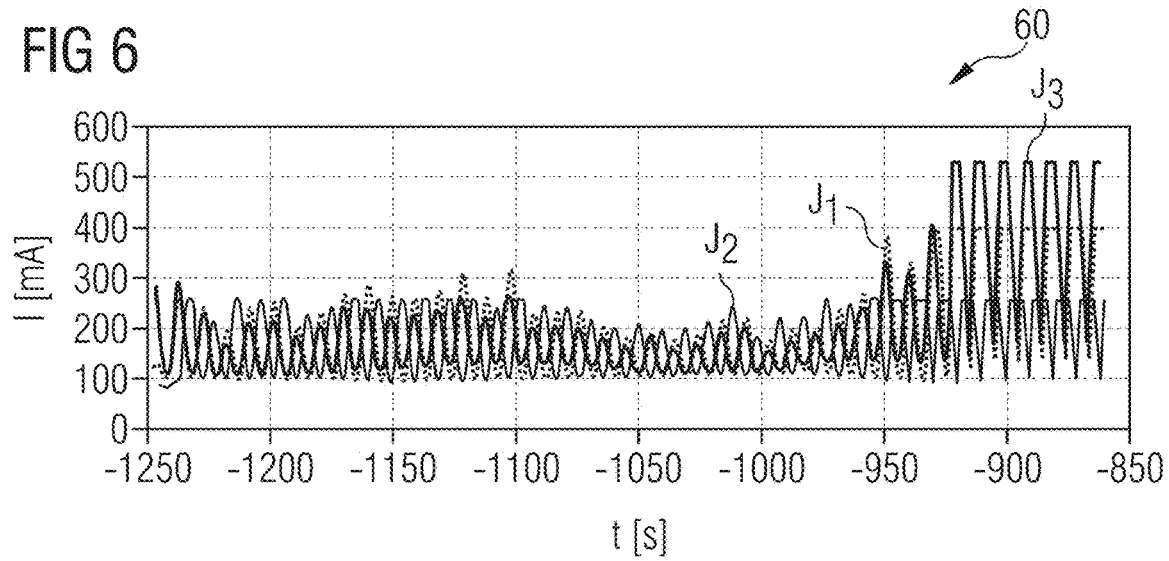
FIG. 6 shows a graph illustrating adjusted tube-current profiles for the initial tube-current profiles shown in FIG. 5.

FIG. 6 shows an illustration 60 of the adjusted tube-current profiles $J_1$, $J_2$, $J_3$. The adjusted tube-current profile $J_1$ is associated with the initial tube-current profile $I_1$, the adjusted tube-current profile $J_2$ is associated with the initial tube-current profile $I_2$, and the adjusted tube-current profile $J_3$ is associated with the initial tube-current profile $I_3$. It can be seen that the amplitudes of the individual tube-current profiles are very similar to one another, even though the center topograms 40b and right-hand topograms 40c shown in FIG. 5 and used for calculating the initial tube-current profiles $I_1$, $I_2$, $I_3$ are erroneous. By employing the method according to an embodiment of the invention, dose differences resulting from erroneous preview acquisitions can thus be corrected in an automated manner.

Finally, it shall be reiterated that the method and devices described above are merely preferred example embodiments, and that the invention can be modified by a person skilled in the art without departing from the scope of the invention insofar as this is defined by the claims. Thus the method and the X-ray imaging apparatus have been described primarily with reference to a system for acquiring medical image data. This does not mean, however, that the invention is limited to use in the medical sector, but in principle can also be applied to the acquisition of images for other purposes. It is mentioned for the sake of completeness that the use of the indefinite article "a" or "an" does not rule out the possibility of there also being more than one of the features concerned. Likewise, the term "unit" does not exclude the possibility that the unit consists of a plurality components, which may also be spatially distributed if applicable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for controlling a tube current for acquiring at least one X-ray image of a region under examination of a subject under examination using an X-ray imaging apparatus, comprising:
   performing a preview acquisition of the region under examination of the subject under examination;
   determining a three-dimensionally modulated X-ray attenuation of the region under examination based upon the preview acquisition;
   determining initial tube-current profiles based upon the three-dimensionally modulated X-ray attenuation determined;
   defining a tolerance band for subsequent real-time modification of tube currents, wherein, based upon initial tube-current profiles, a maximum permitted tube-current profile is determined for which an X-ray tube of the X-ray imaging apparatus does not overheat;

determining an expected value and a maximum value of a potential patient dose based upon the initial tube-current profiles and the tolerance band defined;

measuring an actual X-ray attenuation during acquisition of the at least one X-ray image;

determining adjusted tube-current profiles based upon the actual X-ray attenuation and the initial tube-current profiles; and adjusting the tube current in accordance with the adjusted tube-current profiles determined.

2. The method of claim 1, wherein the preview acquisition includes a topogram of the region under examination of the subject under examination.

3. The method of claim 1, wherein the preview acquisition includes an optical image acquisition of the region under examination of the subject under examination.

4. The method of claim 1, wherein the determining of the three-dimensionally modulated X-ray attenuation includes determining X-ray attenuation vectors.

5. The method of claim 4, wherein the X-ray attenuation vectors in an anterior/posterior direction and in a lateral direction are determined by way of the preview acquisition.

6. The method of claim 5, wherein the initial tube-current profiles are determined based upon the determined X-ray attenuation in the anterior/posterior direction and in the lateral direction.

7. The method of claim 5, wherein the actual X-ray attenuation is measured in the anterior/posterior direction and in the lateral direction.

8. The method of claim 1, wherein a maximum permitted increase in the patient dose, by way of a configurable parameter, is displayed to the operator during the X-ray image acquisition.

9. The method of claim 1, wherein the X-ray attenuation is determined by division of a logarithm of the attenuation data by a linear absorption coefficient of water.

10. The method of claim 1, wherein the adjustment is performed based upon a function for adjusting the initially planned tube currents including an exponential function of a product of the absorption coefficient of water and a difference between the actual patient attenuation and the X-ray attenuation vectors.

11. A tube-current controller for acquiring at least one X-ray image of a region under examination of a subject under examination, comprising:

a controller configured to
control an X-ray radiation source for acquisition of the at least one X-ray image, and
capture raw X-ray data from an X-ray radiation detector;

a preview acquisition controller to control a preview acquisition of the region under examination of the subject under examination;

an X-ray attenuation estimation unit to estimate a three-dimensionally modulated X-ray attenuation based upon the preview acquisition;

a profile definition unit to determine initial tube-current profiles based upon the X-ray attenuation estimated;

a band definition unit to define a tolerance band for real-time modification of tube currents, wherein, based upon the initial tube-current profiles, a maximum permitted tube-current profile is determined for which the X-ray tube does not overheat;

a dose determination unit to determine an expected value for a potential patient dose based upon the initial tube-current profiles, and a maximum value of a potential patient dose based upon the defined tolerance band;

an X-ray attenuation determination unit to determine an actual X-ray attenuation during acquisition of the at least one X-ray image based upon raw X-ray data acquired; and an adjustment unit to determine adjusted tube-current profiles based upon the actual X-ray attenuation and initially planned tube-current profiles, wherein the controller is further configured to adjust the tube current of the X-ray source in accordance with the adjusted tube-current profiles determined.

12. An x-ray imaging apparatus, comprising:
an X-ray radiation source including an X-ray tube;
an X-ray radiation detector; and
the tube-current controller of claim 11.

13. A computed tomography system comprising the X-ray imaging apparatus of claim 12.

14. A non-transitory computer program product storing a computer program, directly loadable into a storage device of an X-ray imaging apparatus, including program segments to perform the method of claim 1 when the computer program is executed in the X-ray imaging apparatus.

15. A non-transitory computer-readable medium, storing program segments, readable and executable by a processor to perform the method of claim 1 when the program segments are executed by the processor.

16. The method of claim 2, wherein the preview acquisition includes an optical image acquisition of the region under examination of the subject under examination.

17. The method of claim 2, wherein the determining of the three-dimensionally modulated X-ray attenuation includes determining X-ray attenuation vectors.

18. The method of claim 17, wherein the X-ray attenuation vectors in an anterior/posterior direction and in a lateral direction are determined by way of the preview acquisition.

19. A non-transitory computer program product storing a computer program, directly loadable into a storage device of an X-ray imaging apparatus, including program segments to perform the method of claim 2 when the computer program is executed in the X-ray imaging apparatus.

20. A non-transitory computer-readable medium, storing program segments, readable and executable by a processor to perform the method of claim 2 when the program segments are executed by the processor.

* * * * *